(12) United States Patent
Hayden et al.

(10) Patent No.: US 11,234,973 B2
(45) Date of Patent: Feb. 1, 2022

(54) USE OF PRIDOPIDINE FOR THE TREATMENT OF FRAGILE X SYNDROME

(71) Applicants: PRILENIA NEUROTHERAPEUTICS LTD., Herzliya (IL); NATIONAL UNIVERSITY OF SINGAPORE, Singapore (SG); AGENCY FOR SCIENCE, TECHNOLOGY AND RESEARCH, Singapore (SG)

(72) Inventors: Michael Hayden, Herzliya (IL); Mahmoud Abdulhossein Pouladi, Singapore (SG)

(73) Assignees: PRILENIA NEUROTHERAPEUTICS LTD., Herzliya (IL); NATIONAL UNIVERSITY OF SINGAPORE, Singapore (SG); Agency for Science, Technology and Research, Connexis (SG)

( * ) Notice: Subject to any disclaimer, the term of this patent is extended or adjusted under 35 U.S.C. 154(b) by 27 days.

(21) Appl. No.: 16/514,167

(22) Filed: Jul. 17, 2019

(65) Prior Publication Data
US 2019/0336488 A1 Nov. 7, 2019

Related U.S. Application Data

(63) Continuation-in-part of application No. PCT/US2018/014169, filed on Jan. 18, 2018.

(60) Provisional application No. 62/448,595, filed on Jan. 20, 2017.

(51) Int. Cl.
*A61K 31/451* (2006.01)
*A61K 9/00* (2006.01)
*A61P 43/00* (2006.01)
*A61K 45/06* (2006.01)

(52) U.S. Cl.
CPC .......... *A61K 31/451* (2013.01); *A61K 9/0053* (2013.01); *A61P 43/00* (2018.01); *A61K 45/06* (2013.01)

(58) Field of Classification Search
CPC ....... A61K 31/451; A61K 45/06; A61P 43/00; A61P 27/06; A61P 25/28
See application file for complete search history.

(56) References Cited

U.S. PATENT DOCUMENTS

| | | |
|---|---|---|
| 6,903,120 B2 | 6/2005 | Sonesson et al. |
| 7,923,459 B2 | 4/2011 | Gauthier et al. |
| 9,012,476 B2 * | 4/2015 | Zimmermann ......... A61P 25/28 514/317 |
| RE46,117 E | 8/2016 | Sonesson et al. |
| 2003/0139423 A1 | 7/2003 | Sonesson et al. |
| 2006/0135531 A1 | 6/2006 | Sonesson et al. |
| 2007/0238879 A1 | 10/2007 | Gauthier et al. |
| 2010/0105736 A1 | 4/2010 | Wikström |
| 2013/0150406 A1 | 6/2013 | Zimmermann et al. |
| 2013/0197031 A1 | 8/2013 | Sonesson |
| 2013/0267552 A1 | 10/2013 | Waters et al. |
| 2014/0315951 A1 | 4/2014 | Sonesson et al. |
| 2014/0147491 A1 | 5/2014 | Glass et al. |
| 2014/0378508 A1 | 12/2014 | Bassan et al. |
| 2015/0202302 A1 | 7/2015 | Licht et al. |
| 2015/0209344 A1 | 7/2015 | Zimmemann et al. |
| 2015/0216850 A1 | 8/2015 | Hayden et al. |
| 2015/0374677 A1 | 12/2015 | Schmidt et al. |
| 2016/0095847 A1 | 4/2016 | Sonesson |
| 2016/0166559 A1 | 6/2016 | Sonesson |
| 2016/0176821 A1 | 6/2016 | Wu et al. |
| 2016/0243098 A1 | 8/2016 | Geva et al. |

FOREIGN PATENT DOCUMENTS

| | | |
|---|---|---|
| WO | WO 2001/046145 A1 | 6/2001 |
| WO | WO 2006/040155 A1 | 4/2006 |
| WO | WO 2008/127188 A1 | 10/2008 |
| WO | WO 2008/133884 A2 | 11/2008 |
| WO | WO 2012/002863 A1 | 1/2012 |
| WO | WO 2013/034622 A1 | 3/2013 |
| WO | WO 2013/086425 A1 | 6/2013 |
| WO | WO 2013/152105 A1 | 10/2013 |
| WO | WO 2014/205229 A1 | 12/2014 |
| WO | WO 2015/112601 A1 | 7/2015 |
| WO | WO 2016/003919 A1 | 1/2016 |
| WO | WO 2016/138130 A1 | 9/2016 |
| WO | WO 2016/138135 A1 | 9/2016 |

OTHER PUBLICATIONS

Cogram et al., Sigma-1 Receptor Agonists as Potential Treatment Options for Autism Spectrum Disorders: Pre-clinical Studies with ANAVEX 2-73 in a Fragile X Model at https://anavex.com//wp-content/uploads/ Sigma-1-Receptor-Agonists-as-Potential-Treatment-Options.pdf (Year: 2016).*
Hampson et al. in Biochemical Pharmacology 81 (2011) 1078-1086 (Year: 2011).*
Squitieri et al. in Journal of Cellular and Molecular Medicine 19(11), 2540-2548 (2015) (Year: 2015).*
Villard et al. in Journal of Psychopharmacology (2011) 25(8): 1101-1117 (Year: 2011).*
Verraragavan et al. in Psychopharmacology (2011) 217(1): 143-151 (Year: 2011).*
Bhattacharyya et al. "Human pluripotent stem cell models of Fragile X syndrome" Molecular and Cellular Neuroscience. Jun. 1, 2016;73:43-51.
CSID:25948790, www.chemspider.com/Chemical-Structure.25948790. html (accessed 23:27, Jul. 15, 2016).
CSID:7971505, www.chemspider.com/Chemical-Structure.7971505. html (accessed 23:33, Jul. 15, 2016).

(Continued)

*Primary Examiner* — Dennis Heyer
(74) *Attorney, Agent, or Firm* — Mark S. Cohen; Pearl Cohen Zedek Latzer Baratz LLP (57) ABSTRACT

The invention provides a method of treating a subject afflicted with fragile X syndrome (FXS) or a FXS related disorder, comprising periodically administering to the subject a pharmaceutical composition comprising an amount of pridopidine effective to treat the subject.

17 Claims, 8 Drawing Sheets

(56) References Cited

OTHER PUBLICATIONS

Doers et al. "iPSC-derived forebrain neurons from FXS individuals show defects in initial neurite outgrowth" Stem cells and development. Mar. 24, 2014;23(15):1777-87.

Geva et al. "Pridopidine activates neuroprotective pathways impaired in Huntington Disease" Human molecular genetics. Jul. 27, 2016;25(18):3975-87.

International Search Report for PCT application No. PCT/US2018/014169 dated Mar. 8, 2018.

Kimura et al., "Sigma-1 receptor enhances neurite elongation of cerebellar granule neurons via TrkB signaling" PloS one. Oct. 8, 2013;8(10):e75760.

Leehey MA. "Fragile X-associated tremor/ataxia syndrome: clinical phenotype, diagnosis, and treatment" Journal of Investigative Medicine. Dec. 1, 2009;57(8):830-6.

Ponten et al. "In vivo pharmacology of the dopaminergic stabilizer pridopidine" European journal of pharmacology. Oct. 10, 2010;644(1-3):88-95.

Telias el al. "Functional deficiencies in fragile X neurons derived from human embryonic stem cells" Journal of Neuroscience. Nov. 18, 2015;35(46). 15295-306.

Timothy et al. Autism and fragile X syndrome: In Seminars in neurology Jul. 2014 (vol. 34, No. 03, pp. 258-265). Thieme Medical Publishers.

European Search Report for EP18741607.8 dated Sep. 30, 2020.

McLennan, Y., et al. Fragile X syndrome. *Current genomics*, 2011, 12.3: 216-224.

Bruno et al. (2019). Brain circuitry, behavior, and cognition: A randomized placebo-controlled trial of donepezil in fragile X syndrome. Journal of Psychopharmacology, 33(8), 975-985.

Sahu et al. (2012). Effectiveness ana safety or donepezil in boys with fragile x syndrome: a double-blind, randomized, controlled pilot study. Journal of Child Neurology, 28(5), 570-575.

Veeraragavan et al. (2011). Modulation of behavioral phenotypes by a muscarinic M1 antagonist in a mouse model of fragile X syndrome. Psychopharmacology, 217(1), 143-151.

Woodard et al. (2007). A placebo double-blind pilot study of dextromethorphan for problematic behaviors in children with autism. Autism, 11(1), 29-41.

\* cited by examiner

USE OF PRIDOPIDINE FOR THE TREATMENT OF FRAGILE X SYNDROME

CROSS REFERENCE TO RELATED APPLICATION

This application is a Continuation-in-Part Application of PCT/US2018/014169, filed 18 Jan. 2018, which claims the benefit of U.S. Provisional Application No. 62/448,595, filed Jan. 20, 2017 which are incorporated in their entirety herein by reference.

BACKGROUND

Fragile X Syndrome

Fragile X syndrome (FXS) is the most common form of inherited intellectual disability and variant of autism spectrum disorder (ASD) (Yu and Berry-Kravis, 2014). FXS is caused by an expansion of a CGG repeat in the 5' UTR of the FMR1 gene that results in its specific hyper-methylation, silencing, and loss of FMR1 protein (FMRP) expression.

Fragile X-associated tremor/ataxia syndrome (FXTAS), an example of a FXS related disorder, is an adult onset neurodegenerative disorder caused by a CGG repeat expansion in the premutation range (55-200) in the FMR1 gene. The main clinical features of FXTAS in older males include problems of movement with cerebellar gait ataxia and action tremor (Leehey 2009).

An effective therapy remains lacking. New effective therapies for FXS and related disorders are needed.

Pridopidine

Pridopidine (4-[3-(methylsulfonyl)phenyl]-1-propyl-piperidine) (formerly known as ACR16) is a drug under development for treatment of Huntington's disease. Pridopidine has been shown to modulate motor activity by either suppressing hyperactivity or enhancing hypoactivity. The neuroprotective properties of pridopidine are suggested to be attributed to its high affinity to the sigma-1 receptor (S1R, binding IC50~100 nM), while the motor activity of pridopidine may be mediated primarily by its low-affinity, antagonistic activity at the dopamine D2 receptor (D2R) (binding IC50~10 μM) (Ponten 2010). Pridopidine shows low-affinity binding to additional receptors in the micromolar range.

The S1R is an endoplasmic reticulum (ER) chaperone protein which is implicated in cellular differentiation, neuroplasticity, neuroprotection and cognitive function in the brain. Recently, transcriptomic analysis of rat striatum showed that pridopidine treatment activates expression of the BDNF, dopamine receptor 1 (D1R), glucocorticoid receptor (GR), and the serine-threonine kinase protein kinase B (Akt)/phosphoinositide 3-kinase (PI3K) pathways, known to promote neuronal plasticity and survival and to be impaired in HD. Moreover, pridopidine gene expression profile showed a reversed pattern of the HD disease gene expression profile in a Q175 knock-in (Q175 KI) HD mouse model (Geva 2016). Pridopidine also enhances secretion of the neuroprotective brain-derived neurotrophic factor (BDNF) in a neuroblastoma cell line, in a S1R-dependent manner (Geva 2016).

SUMMARY OF THE INVENTION

This invention provides a method of treating a subject afflicted with fragile X syndrome (FXS), comprising periodically administering to the subject a pharmaceutical composition comprising an amount of pridopidine, or pharmaceutical acceptable salt thereof, effective to treat the subject.

The invention also provides pridopidine for use in treating a subject afflicted with FXS.

The invention also provides use of pridopidine for the manufacture of a medicament for use in treating a subject afflicted with FXS.

The invention also provides a pharmaceutical composition comprising an effective amount of pridopidine for treating FXS.

The invention also provides a pharmaceutical composition comprising pridopidine for use in treating a subject suffering from FXS.

The invention also provides a package comprising:
a) a pharmaceutical composition comprising an amount of pridopidine; and
b) instructions for use of the pharmaceutical composition to treat a subject afflicted with FXS.

The invention also provides a therapeutic package for dispensing to, or for use in dispensing to, a subject afflicted with FXS, which comprises:
a) one or more unit doses, each such unit dose comprising an amount of pridopidine thereof, wherein the amount of said pridopidine in said unit dose is effective, upon administration to said subject, to treat the subject, and
b) a finished pharmaceutical container therefor, said container containing said unit dose or unit doses, said container further containing or comprising labeling directing the use of said package in the treatment of said subject.

The invention also provides a package comprising:
a) a first pharmaceutical composition comprising an amount of pridopidine and a pharmaceutically acceptable carrier;
b) a second pharmaceutical composition comprising an amount of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine. Sertraline, Citalopram, Paroxetine, Fluvoxamine, Risperidone, Quetiapine, Olanzapine, Trazodone, or Melatonin and a pharmaceutically acceptable carrier; and
c) instructions for use of the first and second pharmaceutical compositions together to treat a subject afflicted with FXS.

The invention also provides a package comprising:
a) a first pharmaceutical composition comprising an amount of pridopidine and a pharmaceutically acceptable carrier:
b) a second pharmaceutical composition comprising an amount of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine. Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, or Melatonin, and a pharmaceutically acceptable carrier; and
c) instructions for use of the first and second pharmaceutical compositions together to treat a subject afflicted with FXS.

The invention also provides a therapeutic package for dispensing to, or for use in dispensing to, a subject afflicted with FXS, which comprises:
a) one or more unit doses, each such unit dose comprising:
  i) an amount of pridopidine and
  ii) an amount of a second pharmaceutical agent selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine. Fluoxetine, Sertraline, Citalopram, Paroxetine, Fluvoxamine, Risperidone, Quetiapine, Olanzapine, Trazodone, and Melatonin wherein the respective amounts of said pridopidine and said second pharmaceutical agent in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

The invention also provides a therapeutic package for dispensing to, or for use in dispensing to, a subject afflicted with FXS, which comprises:

a) one or more unit doses, each such unit dose comprising:
  i) an amount of pridopidine and
  ii) an amount of one or more of a second pharmaceutical agent selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, and Melatonin, wherein the respective amounts of said pridopidine and said one or more of the second pharmaceutical agent in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

BRIEF DESCRIPTION OF THE FIGURES

FIGS. 1A-1B. FXS hESC lacking FMRP expression maintain pluripotency. (1A-1B) Expression of the pluripotency markers in in FXS hESCs as shown by immunocytochemistry (1A) and qRT-PCR (1B). No FMRP (1A) or FMR1 mRNA (1B) is seen in FXS hESCs. In FIG. 1B, levels of FMR1 are represented by the fourth column from the left in each of control and FXS hESCs and are undetectable in FXS hESCs (i.e. absence of fourth column in FXC hESCs).

FIGS. 4A-4C. Human FXS neurons exhibit neurite growth deficits.

(4A) Delineated neurites of control and FXS neurons on day 7 (bright-field).

(4B) Reduced neurite length in FXS (bottom data) compared with control neurons (top data).

(4C) Reduced neurite branch points in FXS (bottom data) compared with control neurons (top data).

DETAILED DESCRIPTION OF THE INVENTION

This invention provides a method of treating a subject afflicted with fragile X syndrome (FXS) or a FXS related disorder, comprising periodically administering to the subject a pharmaceutical composition comprising an amount of pridopidine effective to treat the subject.

Further provided is pridopidine for use in treating a subject afflicted with FXS.

Further provided is use of pridopidine for the manufacture of a medicament for use in treating a subject afflicted with FXS.

Yet further provided is use of pridopidine or a pharmaceutical composition comprising an effective amount of pridopidine for treating FXS.

In an embodiment, the subject is also afflicted with autism spectrum disorder (ASD). In some embodiments the subject is afflicted with FXTAS.

In another embodiment, the amount of pridopidine is effective to reduce the severity of one or more symptoms of FXS in the subject. In another embodiment, the amount of pridopidine is effective to reduce the severity of one or more symptoms of FXTAS in the subject.

In an embodiment, the one or more symptoms of FXS are selected from the group consisting of cognitive impairment, developmental delays, social and behavior problems, anxiety, hyperactive behavior, hypersensitivity to sensory stimuli, altered gastrointestinal function, and seizures. In another embodiment, the symptom is cognitive impairment and the cognitive impairment is an intellectual disability or a learning disability. In another embodiment, the symptom is developmental delays which are development delays of speech and language.

The one or more symptoms of FXTAS in older males include movement impairment with cerebellar gait ataxia and action tremor.

In some embodiments, the method of treatment, the composition and the use include restoring neurite outgrowth in a subject afflicted with FXS or the FXS related disorder.

In an embodiment, between 10-315 mg pridopidine is administered to the patient per day. In another, between 22.5-315 mg pridopidine is administered to the patient per day. In one embodiment, the amount of pridopidine administered is 20 mg/day-90 mg/day. In one embodiment, the amount of pridopidine administered is 90 mg/day-225 mg/day. In one embodiment, the amount of pridopidine administered is 180 mg/day-225 mg/day. In another embodiment, 10 mg, 22.5 mg, 45 mg, 67.5, mg, 90 mg, 100 mg, 112.5 mg, 125 mg, 135 mg, 150 mg, 180 mg, 200 mg, 250 mg, or 315 mg pridopidine is administered to the patient per day. In an embodiment, the amount of pridopidine administered is 45 mg/day. In an embodiment, the amount of pridopidine administered is 90 mg/day. In an embodiment, the amount of pridopidine administered is 180 mg/day. In an embodiment, the amount of pridopidine administered is 225 mg/day.

In an embodiment, the amount of pridopidine is administered by a unit dose of 10 mg, 22.5 mg, 45 mg, 67.5, mg, 90 mg, 100 mg, 112.5 mg, 125 mg, 135 mg, 150 mg, 180 mg, 200 mg, 250 mg, or 315 mg pridopidine.

In an embodiment, the unit dose is administered once daily.

In an embodiment, the unit dose is administered more than once daily. In another embodiment, the unit dose is administered twice per day.

In an embodiment, the pridopidine is in the form of pridopidine hydrochloride.

In one embodiment, the subject has more than 200 CGG repeats on the X chromosome.

In one embodiment, the subject has about 50-200 CGG repeats on the X chromosome and is afflicted with FXTAS.

In an embodiment, the subject is less than 18 years old. In an embodiment, the subject is male. In other embodiments, the subject is female. In an embodiment, the subject is a human patient.

In an embodiment, the periodic administration is oral.

This invention provides a method of treating a subject afflicted with FXS, comprising periodically administering to the subject a pharmaceutical composition comprising an amount of pridopidine and further comprises the administration of a second pharmaceutical agent selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, and Melatonin.

The invention also provides pridopidine for use in treating a subject afflicted with FXS.

The invention also provides pridopidine for the manufacture of a medicament for use in treating a subject afflicted with FXS.

The invention also provides a pharmaceutical composition comprising an effective amount of pridopidine for treating FXS.

The invention also provides a pharmaceutical composition comprising pridopidine for use in treating a subject suffering from FXS.

The invention also provides a package comprising:
a) a pharmaceutical composition comprising an amount of pridopidine; and
b) instructions for use of the pharmaceutical composition to treat a subject afflicted with FXS.

The invention also provides a therapeutic package for dispensing to, or for use in dispensing to, a subject afflicted with FXS, which comprises:
a) one or more unit doses, each such unit dose comprising an amount of pridopidine thereof, wherein the amount of said pridopidine in said unit dose is effective, upon administration to said subject, to treat the subject, and
b) a finished pharmaceutical container therefor, said container containing said unit dose or unit doses, said container further containing or comprising labeling directing the use of said package in the treatment of said subject.

The invention also provides a package comprising:
a) a first pharmaceutical composition comprising an amount of pridopidine and a pharmaceutically acceptable carrier;
b) a second pharmaceutical composition comprising an amount of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, or Melatonin and a pharmaceutically acceptable carrier; and
c) instructions for use of the first and second pharmaceutical compositions together to treat a subject afflicted with FXS.

The invention also provides a package comprising:
a) a first pharmaceutical composition comprising an amount of pridopidine and a pharmaceutically acceptable carrier:
b) a second pharmaceutical composition comprising an amount of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, or Melatonin, and a pharmaceutically acceptable carrier; and
c) instructions for use of the first and second pharmaceutical compositions together to treat a subject afflicted with FXS.

The invention also provides a therapeutic package for dispensing to, or for use in dispensing to, a subject afflicted with FXS, which comprises:
a) one or more unit doses, each such unit dose comprising:
 i) an amount of pridopidine and
 ii) an amount of a second pharmaceutical agent selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, and Melatonin
 wherein the respective amounts of said pridopidine and said second pharmaceutical agent in said unit dose are effective, upon concomitant administration to said subject, to treat the subject, and
b) a finished pharmaceutical container therefor, said container containing said unit dose or unit doses, said container further containing or comprising labeling directing the use of said package in the treatment of said subject.

The invention also provides a therapeutic package for dispensing to, or for use in dispensing to, a subject afflicted with FXS, which comprises:
a) one or more unit doses, each such unit dose comprising:
 i) an amount of pridopidine and
 ii) an amount of one or more of a second pharmaceutical agent selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, and Melatonin, wherein the respective amounts of said pridopidine and said one or more of the second pharmaceutical agent in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

Combinations of the above-described embodiments are also within the scope of the invention. The "second pharmaceutical composition" as referred to herein comprises an amount of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, or Melatonin, or any combination thereof and a pharmaceutically acceptable carrier.

The "second pharmaceutical agent" as described herein is selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, and Melatonin, and any combination thereof, and optionally includes a pharmaceutically acceptable carrier.

For the foregoing embodiments, each embodiment disclosed herein is contemplated as being applicable to each of the other disclosed embodiments. For instance, the elements recited in the method embodiments can be used in the pharmaceutical composition, package, and use embodiments described herein and vice versa.

Terms

As used herein, and unless stated otherwise, each of the following terms shall have the definition set forth below.

The articles "a", "an" and "the" are non-limiting. For example, "the method" includes the broadest definition of the meaning of the phrase, which can be more than one method.

As used herein, "administering to the subject" means the giving of, dispensing of, or application of medicines, drugs, or remedies to a subject to relieve, cure or reduce the symptoms associated with a disease, disorder or condition, e.g., a pathological condition. Oral administration is one way of administering the instant compounds to the subject.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times a week and so on, etc.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine base in a preparation is 90 mg, regardless of the form of the preparation. Thus, when in the form of a salt, e.g. pridopidine hydrochloride salt, the weight of the salt form necessary to provide a dose of 90 mg pridopidine would be greater than 90 mg due to the presence of the salt.

As used herein, a "unit dose", "unit doses" and "unit dosage form(s)" mean a single drug administration entity/entities.

As used herein, "about" in the context of a numerical value or range means±10% of the numerical value or range recited or claimed.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat cognitive deficit. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, to "treat" or "treating" encompasses, e.g., inducing inhibition, regression, or stasis of a disorder and/or disease, e.g. FXS or related disorder, or alleviating, lessening, suppressing, inhibiting, reducing the severity of, eliminating or substantially eliminating, or ameliorating a symptom of the disease or disorder.

As used herein, "inhibition" of disease progression or disease complication in a subject means preventing, delaying or reducing the disease progression and/or disease complication in the subject. This includes, for example, delaying the progression of one of more symptoms in the subject, including but not limited to delaying the progression of: cognitive impairment, intellectual disability, learning disabilities (e.g., having difficulty learning new skills), developmental delays (e.g., not sitting, walking, or talking at the same time as other children the same age), social and behavior problems (e.g., making eye contact, anxiety, trouble paying attention, hand flapping, acting and speaking without thinking, and being very active), anxiety and hyperactive behavior, hypersensitivity to sensory stimuli, altered gastrointestinal function, autistic symptoms (e.g., shyness, poor eye contact, and social anxiety in mild cases to hand flapping, hand biting and preservative speech in the severely affected), attention deficit and hyperactivity, behavioral disturbances (e.g., irritability, aggression and self-injurious behaviors), seizures, obsessive-compulsive behavior and altered gastrointestinal function.

A "symptom" associated with FXS includes any clinical or laboratory manifestation associated with FXS and is not limited to what the subject can feel or observe. Symptoms of FXS include but are not limited to cognitive impairment, intellectual disability, learning disabilities (e.g., having difficulty learning new skills), developmental delays (e.g., not sitting, walking, or talking at the same time as other children the same age), social and behavior problems (e.g., making eye contact, anxiety, trouble paying attention, hand flapping, acting and speaking without thinking, and being very active), anxiety and hyperactive behavior, hypersensitivity to sensory stimuli, altered gastrointestinal function, autistic symptoms (e.g., shyness, poor eye contact, and social anxiety in mild cases to hand flapping, hand biting and preservative speech in the severely affected), attention deficit and hyperactivity, behavioral disturbances (e.g., irritability, aggression and self-injurious behaviors), seizures, obsessive-compulsive behavior and altered gastrointestinal function.

As used herein, "a subject afflicted with FXS" means a subject diagnosed as suffering from FXS. In an embodiment, the subject is diagnosed by the FMR1 DNA Test. In some embodiments the subject is diagnosed with a FXS related disorder, for example FXTAS.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

As used herein, "pridopidine" means pridopidine base or a pharmaceutically acceptable salt thereof, as well as its analogs or its derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. In certain embodiments, pridopidine is a pharmaceutically acceptable salt, such as the HCl salt or tartrate salt. Preferably, in any embodiments of the invention as described herein, the pridopidine is in the form of its hydrochloride salt.

"Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials.

Deuterium-enrichment when used in connection with a percentage refers to the percentage of incorporation of deuterium at a given position in a molecule in the place of hydrogen. For example, deuterium enrichment of 1% at a given position means that 1% of molecules in a given sample contain deuterium at the specified position. Deuterium-enrichment can be determined using conventional analytical methods known to one of ordinary skill in the art, including mass spectrometry and nuclear magnetic resonance spectroscopy.

The invention also includes any analog of pridopidine or combination of pridopidine with one or more of its analogs.

In one embodiment, a pridopidine analog is represented by following structures or salts thereof:

(1)

(2)

(3)

(4)

(5)

(6) or (7)

As used herein, "combination" means an assemblage of reagents for use in therapy either by simultaneous or contemporaneous administration. Simultaneous administration refers to administration of an admixture (whether a true mixture, a suspension, an emulsion or other physical combination) of the pridopidine and the second compound. In this case, the combination may be the admixture or separate containers of the pridopidine and the second compound that are combined just prior to administration. Contemporaneous administration refers to the separate administration of the pridopidine and the second compound at the same time, or at times sufficiently close together that an additive or preferably synergistic activity relative to the activity of either the pridopidine or the second compound alone is observed.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine therapy to a patient already receiving donepezil therapy.

A dosage unit as used herein may comprise a single compound or mixtures of compounds thereof. A dosage unit can be prepared for oral dosage forms, such as tablets, capsules, pills, powders, and granules.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

A "salt thereof" is a salt of the instant compound which has been modified by making acid or base salts of the compound. The term "pharmaceutically acceptable salt" in this respect, refers to the relatively non-toxic, inorganic and organic acid or base addition salts of compound of the present invention suitable for pharmaceutical use. Pharmaceutically acceptable salts may be formed by procedures well known and described in the art. One means of preparing such a salt is by treating a compound of the present invention with an inorganic base.

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of Remington's Pharmaceutical Sciences (Maack Publishing Co., Easton, Pa.).

By any range disclosed herein, it is meant that all hundredth, tenth, and integer unit amounts within the range are provided by the invention and specifically disclosed as part of the invention. Thus, for example, "10 mg to 315.0 mg" or "10 mg-315.0 mg" means that 10.0 mg, 10.1 mg, 10.2 mg, . . . 22.0, 22.1 mg, 22.2 mg, 22.3 mg, 22.4 mg, etc. up to 315.0 mg unit amounts are included as embodiments of this invention.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Human Fragile X Syndrome Embryonic Stem Cells (FXS hESCs)

Human pluripotent stem cells are emerging as a power tool to study neurological diseases, including ASDs (Bhattacharyya 2015; Telias 2015; Doers 2015). Human Fragile X Syndrome embryonic stem cells (FXS hESCs) were used to uncover neuronal developmental deficits in human FXS neurons. These neuronal developmental deficits can serve as endpoints to assess the therapeutic potential of candidate compounds. The deficits in FXS hESCs neurons (FXS neurons) and the effect of pridopidine in FXS neurons are described below. Control cells used were a human Embryonic Stem (ES) cell line.

Figure 1A:
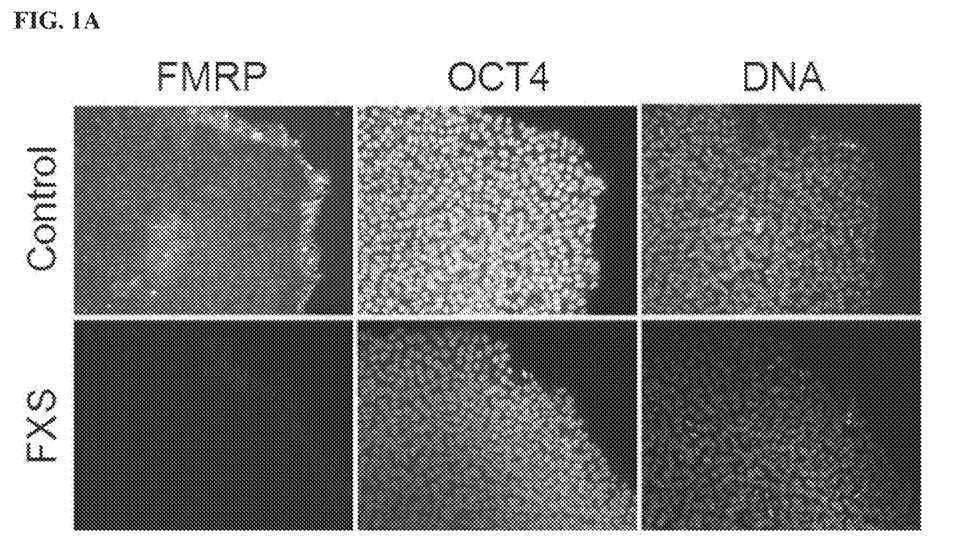
Figure 1B:
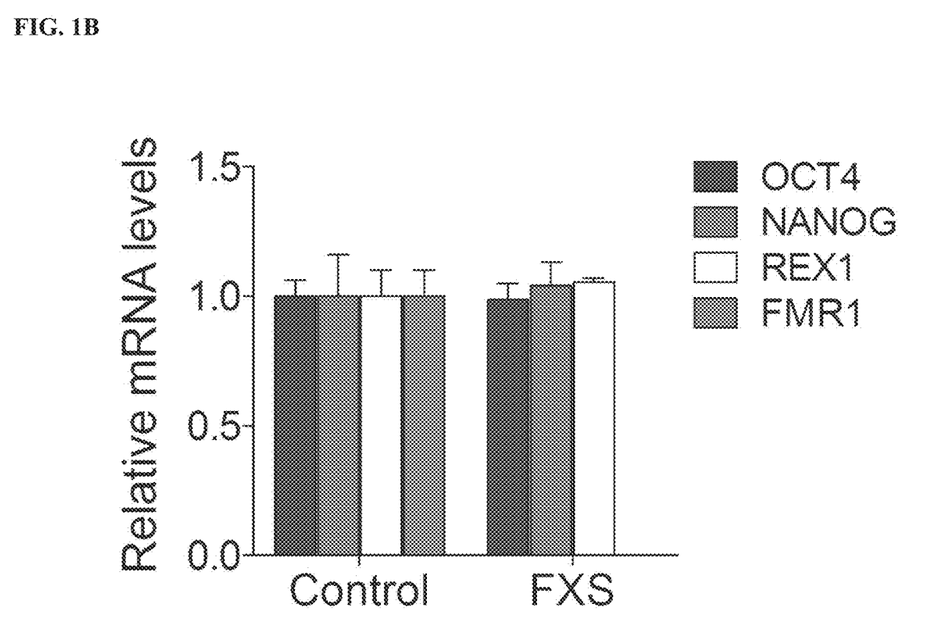

FXS hESCs maintain pluripotency despite the lack of FMRP and FMR1 expression as shown by expression of the pluripotency markers OCT4, NANOG, and REX1 (FIGS. 1A and 1B). DAPI staining was used to detect cell nuclei and is identified herein as "DNA".

Figure 2A:
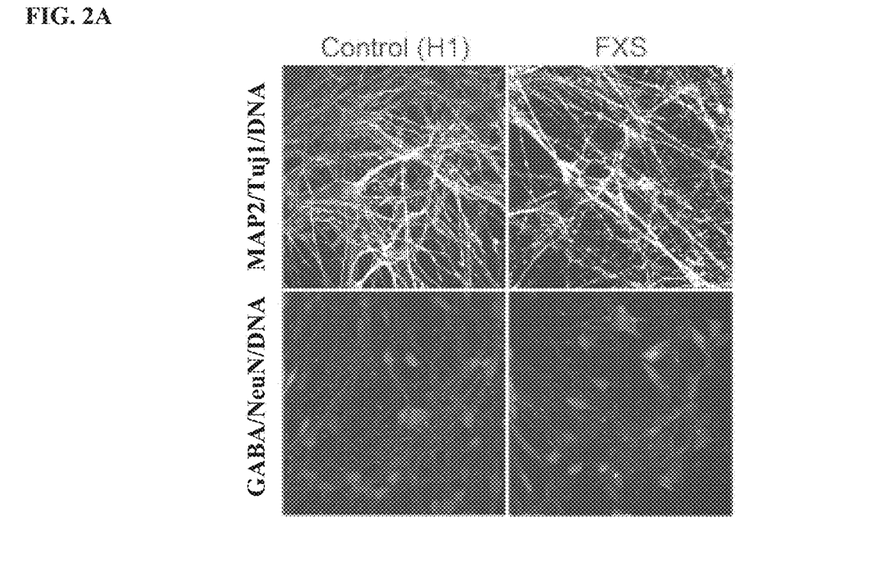
FIGS. 2A-2C. FXS hESCs can be differentiated efficiently into mature neurons. (2A-2C) FXS hESC can be differentiated efficiently into neurons of excitatory and inhibitory identity as shown by expression of MAP2, Tuj-1, GABA, and NeuN protein (2A) and MAP2, VGLUT2, GAD67, SYP, and SYN mRNA (2B). On day 21 of differentiation, approximately 80% of the cells were of neuronal identity (2C).
Figure 2B:
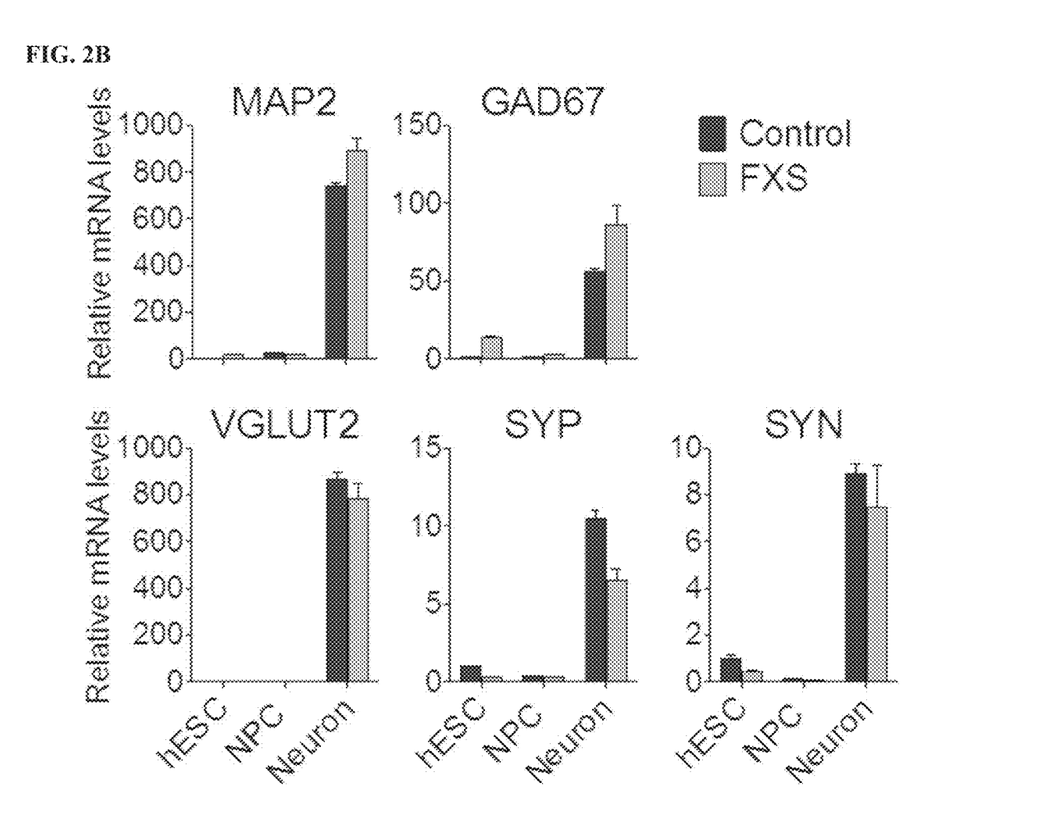
Figure 2C:
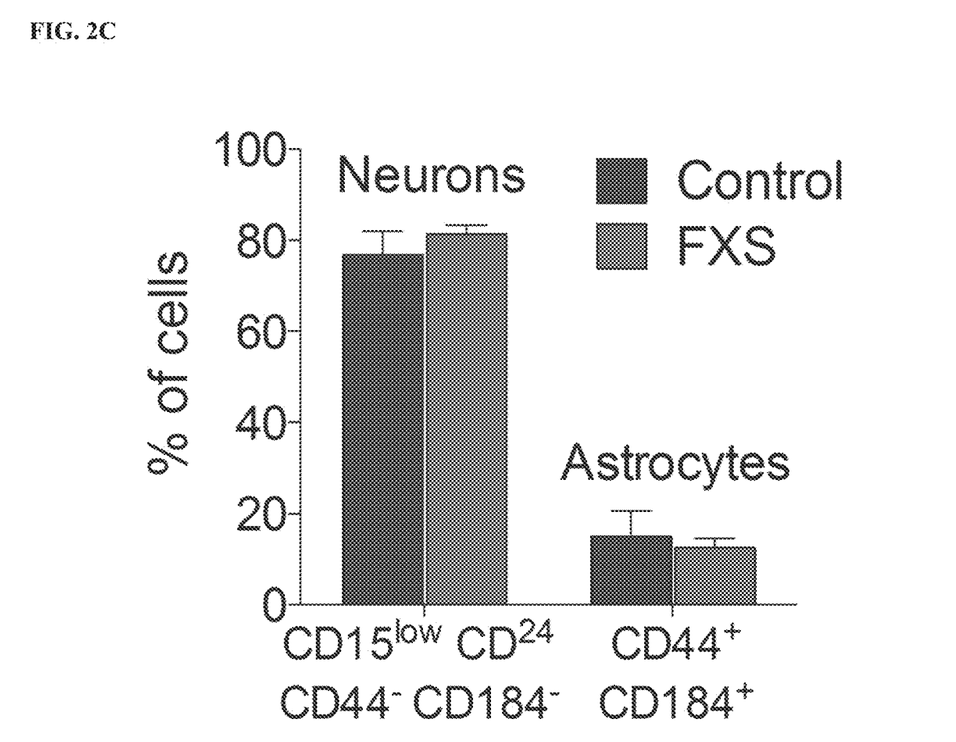

FXS hESCs were differentiated into a neuronal population (FIG. 2A) with an efficiency comparable to control hESCs, as shown by the expression levels of the neuronal markers MAP2, GAD67, VGLUT2, SYP, and SYN (FIG. 2B), and the high proportion of neuronal cells, about 80%, as determined by CD markers (FIG. 2C). FIG. 2A upper panels show MAP2/Tuj-1/DNA immunostaining; lower panels show GABA/NeuN/DNA immunostaining. FIG. 2B shows relative mRNA levels of neuronal marker labeled in hESC control cells, NPC and neuronal cells.

Figure 3A:
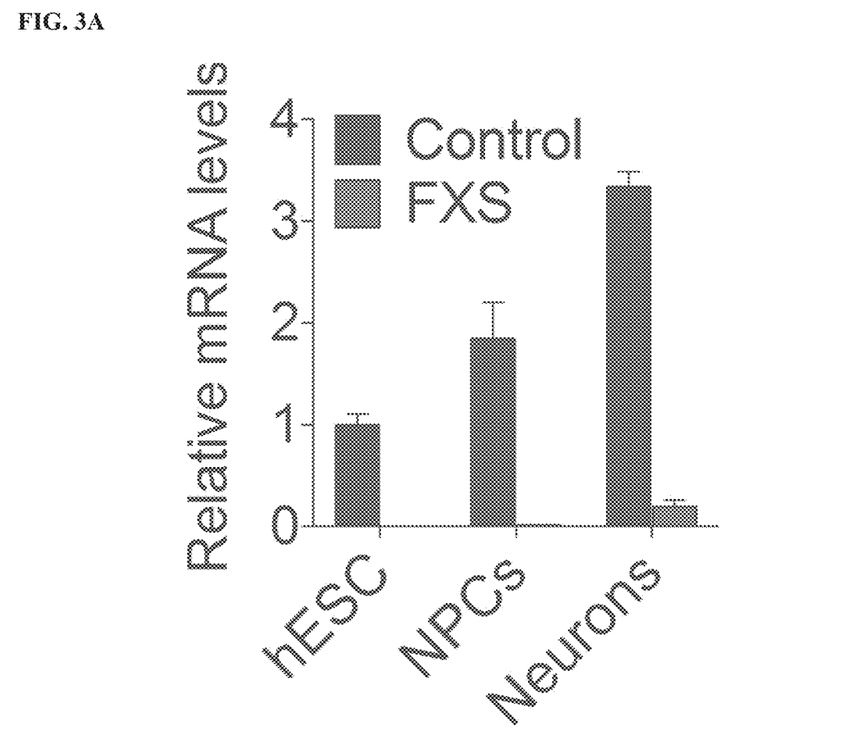
FIGS. 3A and 3B. FMR1 remains silenced following neuronal differentiation of FXS hESCs. No expression of FMR1 mRNA (3A) or FMRP (protein encoded by FMR1 gene) (3B) is seen in neural progenitor cells (NPCs) or neurons differentiation from FXS hESCs.
Figure 3B:
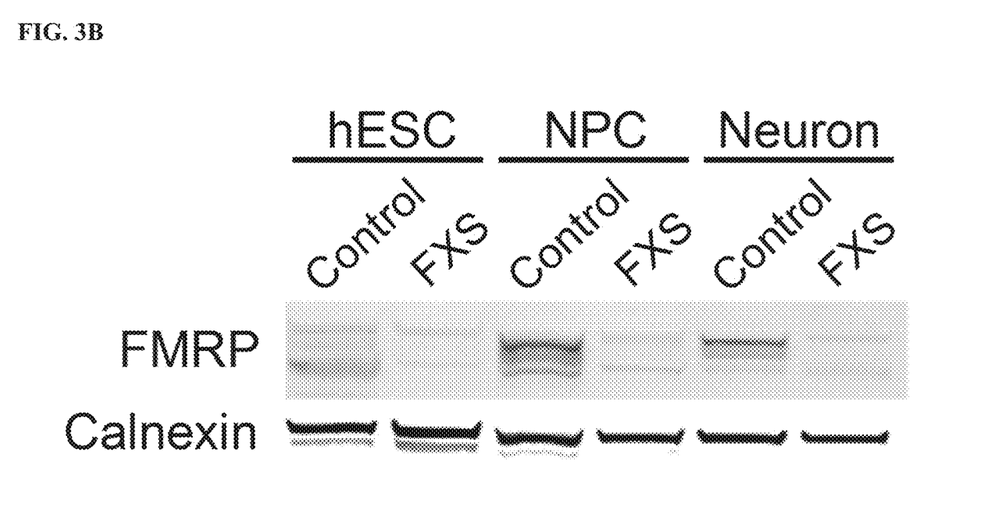

FIG. 3 shows that FMR1 remains silenced following differentiation into neural progenitor cells (NPCs) and neurons. FIGS. 3A and 3B show that no expression of FMR1 mRNA (3A) or FMRP protein (3B) was seen in NPCs or neurons differentiated from FXS hESCs.

Figure 4A:
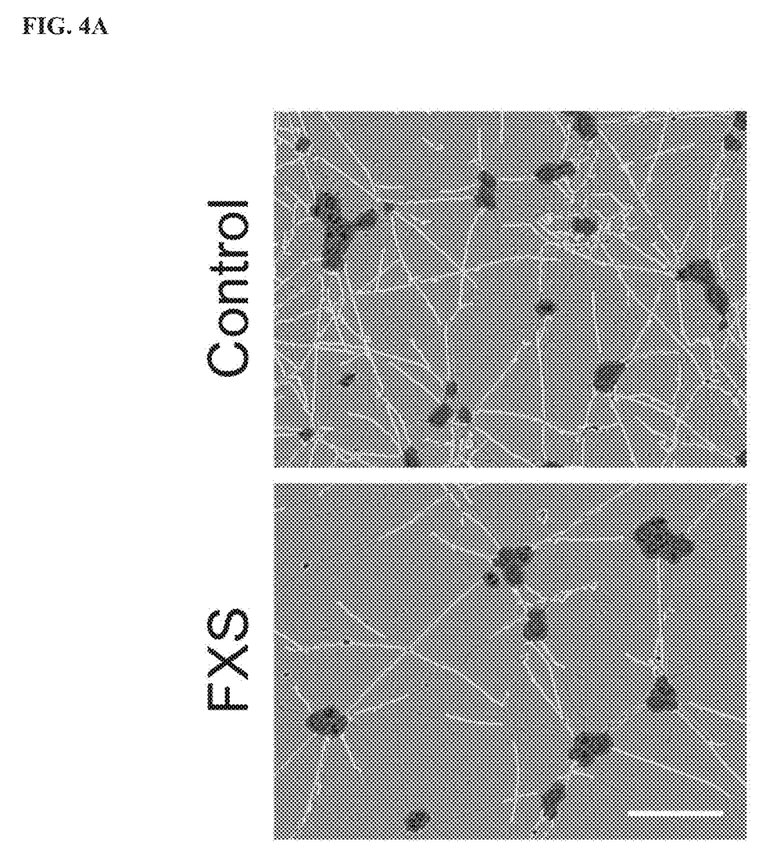
Figure 4B:
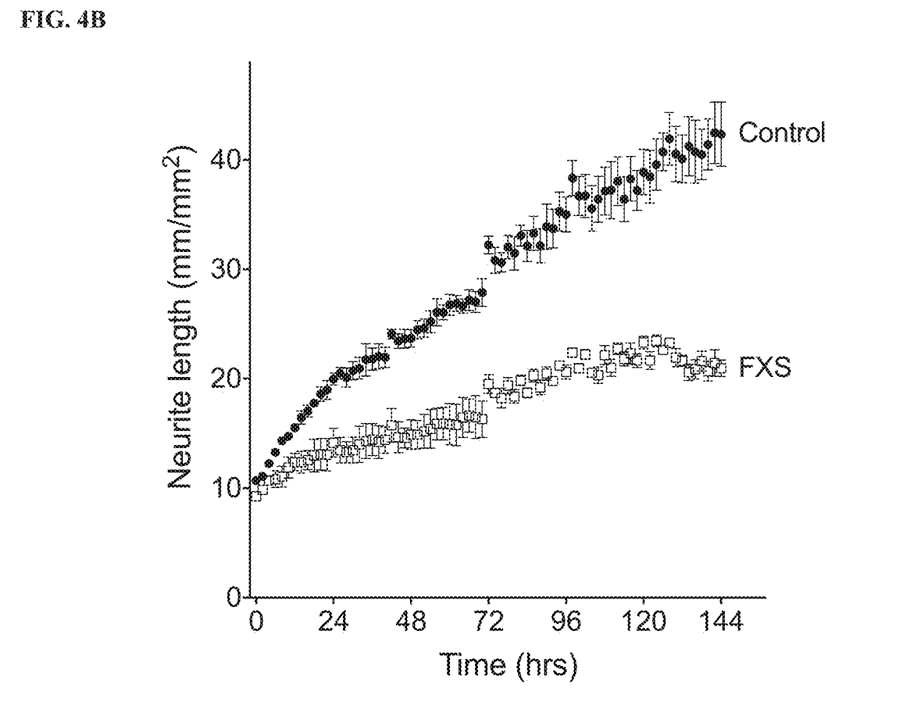
Figure 4C:
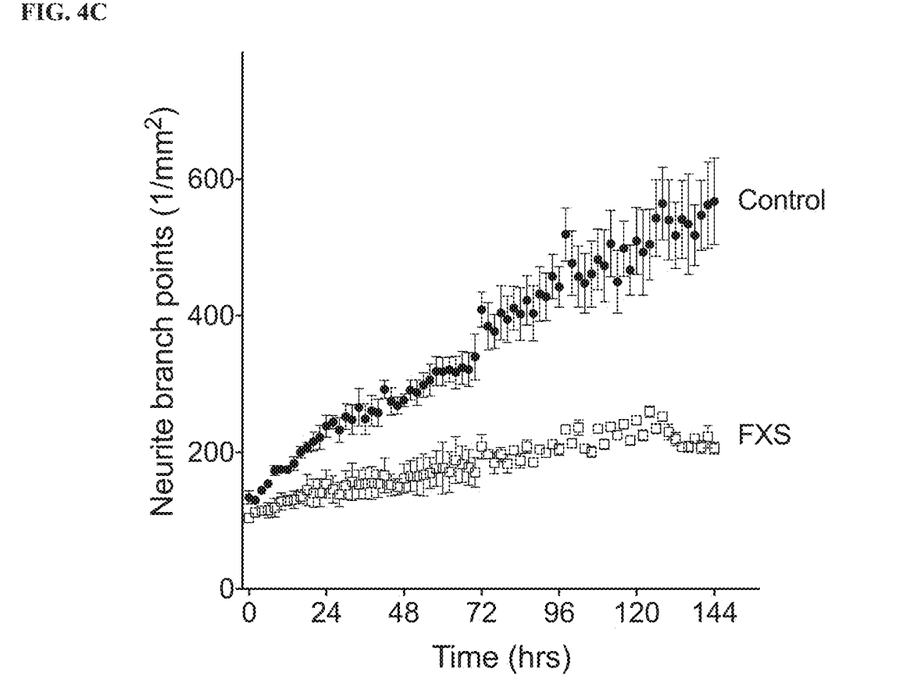

Neurite growth is a surrogate of neuronal development and maturation. FIGS. 4A, 4B and 4C show that neurite length and branch points are significantly reduced in FXS neurons, suggesting that neurite growth is defective in human FXS neurons. FIG. 4A shows delineated neurites of control and FXS neurons on day 7 (bright-field microscopy). There are fewer outgrowths in the FXS neurons compared to control neurons. FIG. 4B shows reduced neurite length in FXS neurons compared to control neurons. FIG. 4C shows reduced neurite branch points in FXS neurons compared to control neurons.

Figure 5:
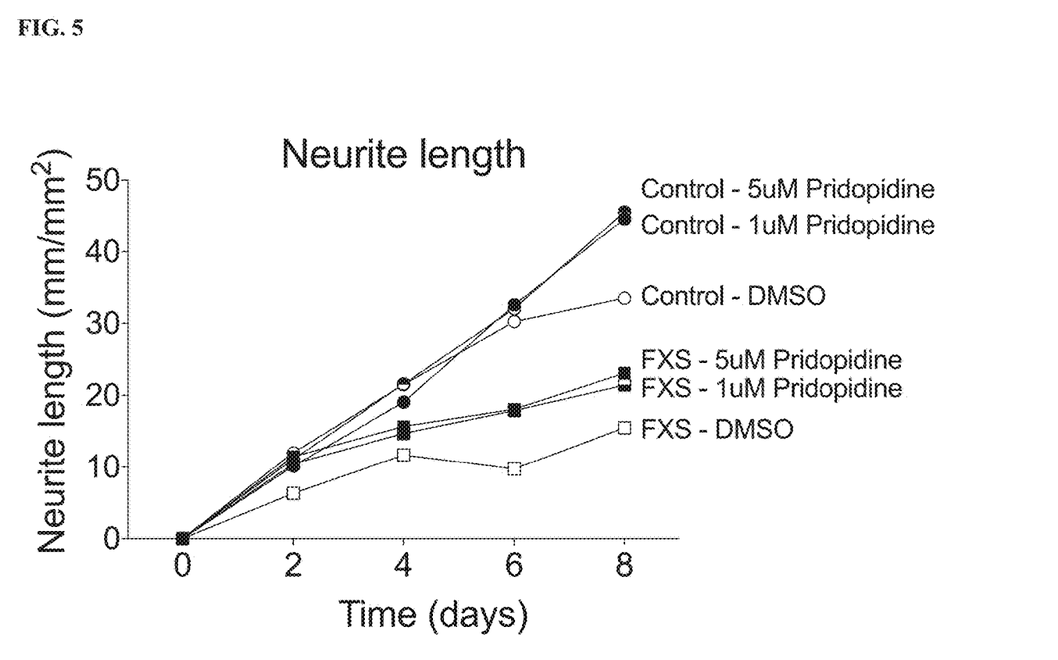
FIG. 5. Pridopidine treatment improves neurite growth in human FXS neurons. Growth of neurites of control cells and FXS hESC-derived neurons treated with 1 uM, 5 uM, or vehicle (DMSO) was assessed over an 8-day period. Pridopidine improved neurite deficits in human FXS neurons at both doses tested.

Sigma-1 receptor activity has been shown to influence neurite growth in neurons (Kimura et al. 2013). FIG. 5 demonstrates the effect of pridopidine treatment on longitudinal neurite growth in human FXS neurons and control neurons. Pridopidine treatment led to a significant improvement in neurite growth in FXS neurons at both 1 uM (half filled square) and 5 uM (solid square). Open squares show data from DMSO treated FXS neurons. Circles show data from DMSO treated (open circle), 1 uM (solid circle) and 5 uM pridopidine (half filled circle) treated control cells. The present example demonstrates that pridopidine restores the neurite outgrowth deficits in human FXS neurons. This example demonstrates that pridopidine has therapeutic value in the treatment of FXS.

Figure 6A:
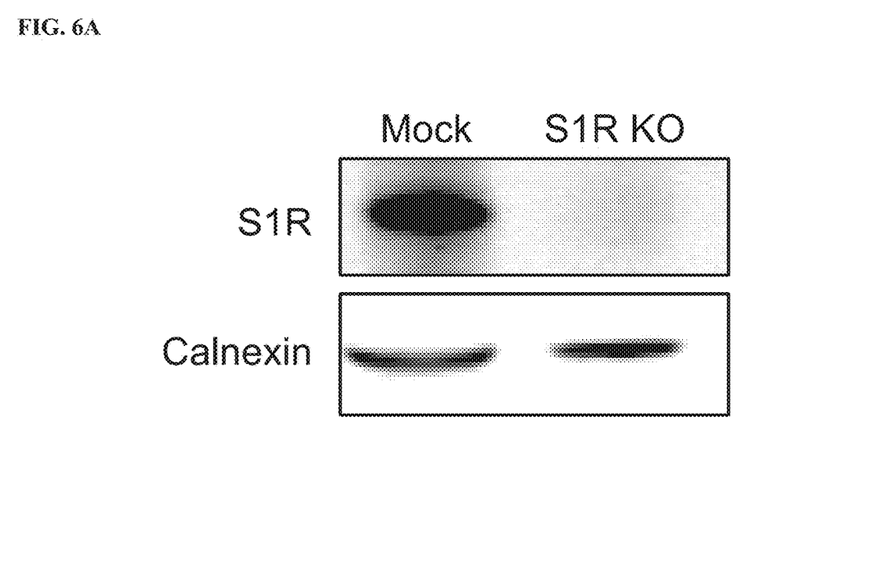
FIGS. 6A-6C. Genetic and pharmacological inactivation of S1R abolish pridopidine-mediated improvements in neurite outgrowth in FXS neurons. Effective inactivation of S1R gene and loss of its protein product was confirmed by western blot (FIG. 6A). Improvement in neurite outgrowth observed in FXS neurons treated with pridopidine was abolished in FXS neurons in which S1R was inactivated (S1RKO) (FIG. 6B). Co-administration of NE-100 blocked the effect of pridopidine on neurite outgrowth in FXS neurons (FIG. 6C).
Figure 6B:
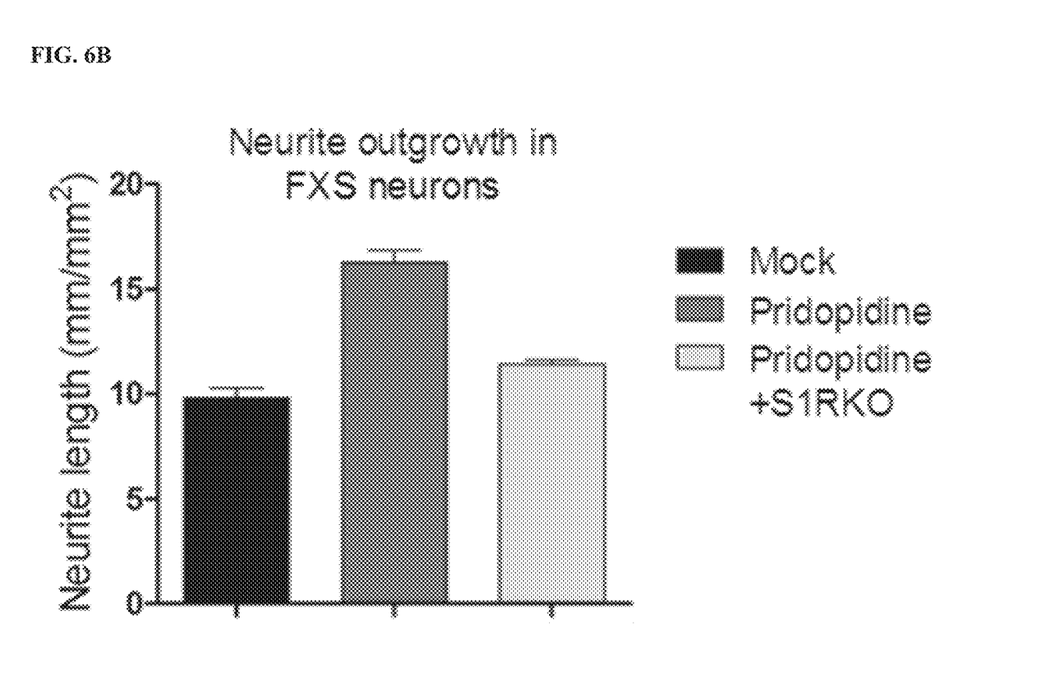

Example 2: Genetic and Pharmacological Inactivation of Sigma-1 Receptor Abolish Pridopidine-Mediated Improvements in Neurite Outgrowth in FXS Neurons To investigate whether the rescue of neurite outgrowth deficits in FXS neurons following pridopidine treatment is mediated via sigma-1 receptor (S1R), virally-delivered Cas9 was used to target and inactivate S1R in FXS NPC prior to neuronal differentiation. Effective inactivation of S1R gene and loss of its protein product was confirmed by western blot (FIG. 6A). The improvement in neurite outgrowth observed in FXS neurons treated with 100 nM pridopidine for 24 hrs was abolished in FXS neurons in which S1R was inactivated (S1RKO) (FIG. 6B).

Figure 6C:
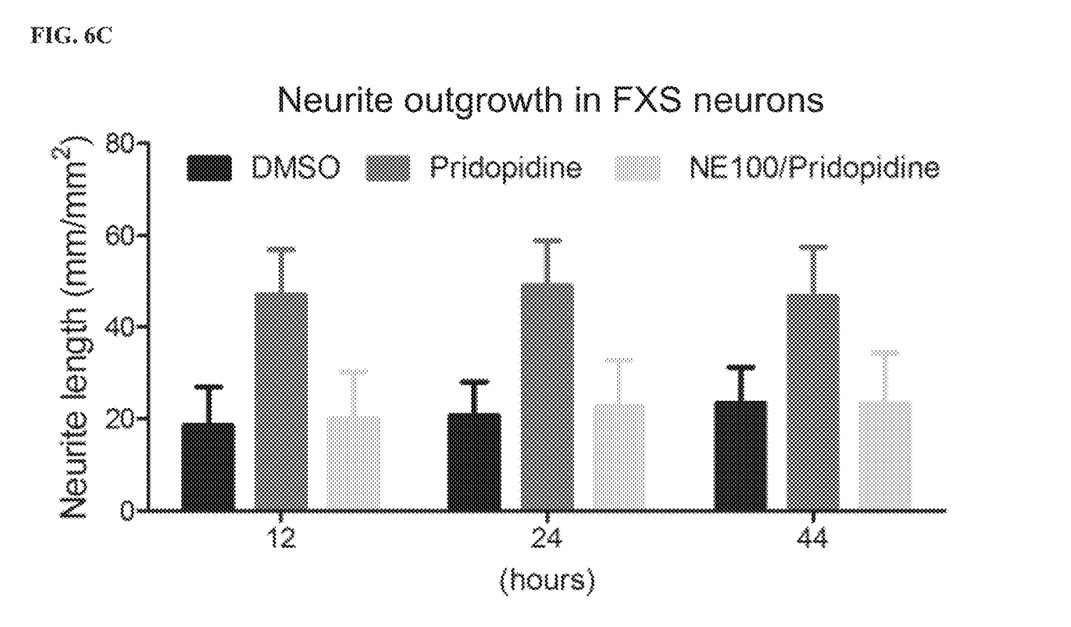

The effect of a pharmacological inhibitor of S1R on pridopidine-mediated neurite outgrowth improvements in FXS neurons was further tested. Co-administration of NE-100 (1 µM), an S1R antagonist, blocked the effect of pridopidine on neurite outgrowth in FXS neurons (FIG. 6C; light gray columns to right of each data set).

These results support a role for S1R in mediating the effects of pridopidine on neurite outgrowth deficits in FXS neurons.

Example 3: Assessment of Efficacy of Pridopidine for Treating Patients Afflicted with FXS Periodic (e.g., daily or twice daily) oral administration of pridopidine is effective in treating human patients afflicted with FXS. The human patients are pediatric patients or adult patients. Periodic (e.g., daily or twice daily) oral administration of pridopidine is effective to treat the subject suffering from FXS.

A pridopidine composition as described herein is administered orally to a subject suffering from FXS. The administration of the composition is effective to treat the subject suffering from FXS.

Example 4: Assessment of Efficacy of Pridopidine for Treating Patients Afflicted with FXS Periodic (e.g., daily or twice daily) oral administration of pridopidine is effective in treating human patients afflicted with a FXS related disorder. The human patients are pediatric patients or adult patients. Periodic (e.g., daily or twice daily) oral administration of pridopidine is effective to treat the subject suffering from a FXS related disorder.

A pridopidine composition as described herein is administered orally to a subject suffering from a FXS related disorder. The administration of the composition is effective to treat the subject suffering from the FXS related disorder.

REFERENCES

Bhattacharyya, A. & Zhao, X. Human pluripotent stem cell models of Fragile X Syndrome. *Mol Cell Neurosci.* (2015).

Doers M E, et al. iPSC-derived forebrain neurons from FXS individuals show defects in initial neurite outgrowth. *Stem Cells Dev.* (2014) 23(15):1777-87.

Geva, M. et al. Pridopidine activates neuroprotective pathways impaired in Huntington Disease. *Hum Molec. Gen.*, (2016). 25(18):3975-3987.

Kimura, Y. et al., Sigma-1 receptor enhances neurite elongation of cerebellar granule neurons via TrkB signaling. *PLoS ONE* (2013) 8, e75760.

Leehey M A. Fragile X-associated Tremor/Ataxia Syndrome (FXTAS): Clinical Phenotype, Diagnosis and Treatment. *J Investigative Medicine* (2009) 57(8):830-836.

Ponten H, Kullingsjö J, Lagerkvist S, Martin P, Pettersson F, Sonesson C, Waters S, Waters N. In vivo pharmacology of the dopaminergic stabilizer pridopidine. *Eur J Pharmacol.* (2010) 644(1-3):88-95.

Telias M, et al. Functional Deficiencies in Fragile X Neurons Derived from Human Embryonic Stem Cells. *J Neurosci.* (2015) 35(46):15295-306.

Yu, T. W. & Berry-Kravis, E. Autism and fragile X syndrome. *Semin Neurol* (2014) 34, 258-265.

CSID:25948790, www.chemspider.com/Chemical-Structure.25948790.html (accessed 23:27, Jul. 15, 2016).
CSID:7971505, wwvw.chemspider.com/Chemical-Structure.7971505.html (accessed 23:33, Jul. 15, 2016).
U.S. Pat. No. 6,903,120, issued Jun. 7, 2005 (Sonesson, et al.)
U.S. Pat. No. 7,923,459, issued Apr. 12, 2011 (Gauthier, et al.)

What is claimed is:

1. A method of treating a subject afflicted with fragile X syndrome (FXS), comprising administering to the subject a pharmaceutical composition comprising an amount of pridopidine or pharmaceutical acceptable salt thereof, effective to treat the subject.

2. The method of claim 1, wherein the subject is also afflicted with autism spectrum disorder (ASD).

3. The method of claim 1, wherein the amount of pridopidine is effective to reduce the severity of one or more symptoms of FXS in the subject.

4. The method of claim 3, wherein the one or more symptoms are selected from the group consisting of cognitive impairment, developmental delays, social and behavior problems, anxiety, hyperactive behavior, hypersensitivity to sensory stimuli, altered gastrointestinal function, and seizures.

5. The method of claim 4, wherein the symptom is cognitive impairment and the cognitive impairment is an intellectual disability or a learning disability.

6. The method of claim 4, wherein the symptom is developmental delays which are development delays of speech and language.

7. The method of claim 1, wherein between 10-315 mg pridopidine is administered to the patient per day.

8. The method of claim 7, wherein the pridopidine is administered once daily.

9. The method of claim 7, wherein pridopidine is administered more than once daily.

10. The method of claim 9, wherein the pridopidine is administered twice per day.

11. The method of claim 1, wherein the subject has more than 200 CGG repeats on the X chromosome.

12. The method of claim 1, wherein the subject is less than 18 years old.

13. The method of claim 1, wherein the subject is human.

14. The method of claim 1, wherein the administration is oral.

15. The method of claim 1, wherein the pridopidine is in the form of pridopidine hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt thereof.

16. The method of claim 1, further comprising the administration of a second pharmaceutical agent selected from the group consisting of Carbamazepine, Valproic acid, Divalproex, Lithium carbonate, Gabapentin, Lamotrigine, Topiramate, Tiagabine, Vigabatrin, Phenobarbital, Primidone, Phenytoin, Methylphenidate, Dextroamphetamine, L-acetylcarnitine, Venlafaxine, Nefazodone, Amantadine, Folic acid, Clonidine, Guanfacine, Fluoxetine, Sertraline, Citalopram, Paroxetine, Fluvoxamine, Risperidone, Quetiapine, Olanzapine, Trazodone, and Melatonin.

17. The method of claim 4, wherein the developmental delay is due to cognitive impairment, social behavior problems, speech and language delay or combination thereof.

* * * * *